United States Patent
Yun et al.

(10) Patent No.: US 11,603,338 B2
(45) Date of Patent: Mar. 14, 2023

(54) REACTORS FOR PREPARING VALUABLE HYDROCARBONS AND HYDROGEN FROM METHANE THROUGH NON-OXIDATIVE PYROLYSIS

(71) Applicant: SK Innovation Co., Ltd., Seoul (KR)

(72) Inventors: Dongmin Yun, Daejeon (KR); Juhwan Im, Daejeon (KR); Dokyoung Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 175 days.

(21) Appl. No.: 17/218,683

(22) Filed: Mar. 31, 2021

(65) Prior Publication Data

US 2021/0309589 A1    Oct. 7, 2021

(30) Foreign Application Priority Data

Apr. 1, 2020    (KR) .................. 10-2020-0039791

(51) Int. Cl.
*C07C 2/78*    (2006.01)
*B01J 6/00*    (2006.01)
*C01B 3/24*    (2006.01)
*C01B 3/56*    (2006.01)

(52) U.S. Cl.
CPC ................ *C07C 2/78* (2013.01); *B01J 6/008* (2013.01); *C01B 3/24* (2013.01); *C01B 3/56* (2013.01); *C01B 2203/0272* (2013.01); *C01B 2203/042* (2013.01); *C01B 2203/048* (2013.01); *C01B 2203/085* (2013.01); *C01B 2203/0833* (2013.01); *C01B 2203/1241* (2013.01)

(58) Field of Classification Search
CPC .......... C07C 2/78; C07C 11/02; C07C 11/24; C07C 15/04; C07C 15/24; C07C 9/06; B01J 6/008; B01J 19/0013; B01J 19/14; B01J 19/244; B01J 19/243; B01J 12/005; B01J 2219/00072; B01J 2219/00094; B01J 2219/00157; B01J 2219/00761; B01J 2219/00132; C01B 3/24; C01B 3/56; C01B 2203/0272; C01B 2203/042; C01B 2203/048; C01B 2203/0833; C01B 2203/085; C01B 2203/1241; C01B 3/26; C10G 50/00

See application file for complete search history.

(56) References Cited

U.S. PATENT DOCUMENTS

2018/0296974 A1*   10/2018   Wachsman ................ C07C 2/76

FOREIGN PATENT DOCUMENTS

KR   1020180113448 A   10/2018

* cited by examiner

*Primary Examiner* — Steven J Bos
*Assistant Examiner* — Syed T Iqbal
(74) *Attorney, Agent, or Firm* — The Webb Law Firm

(57) ABSTRACT

According to this disclosure, there is provided a pyrolysis reaction system and a direct non-oxidative methane coupling process using the same by which it is possible to reach the selectivity for good $C_{\leq 10}$ hydrocarbons and at the same time to inhibit coke from being generated while a good methane conversion is maintained during direct conversion of methane into $C_{2+}$ hydrocarbons through non-oxidative pyrolysis.

20 Claims, 1 Drawing Sheet

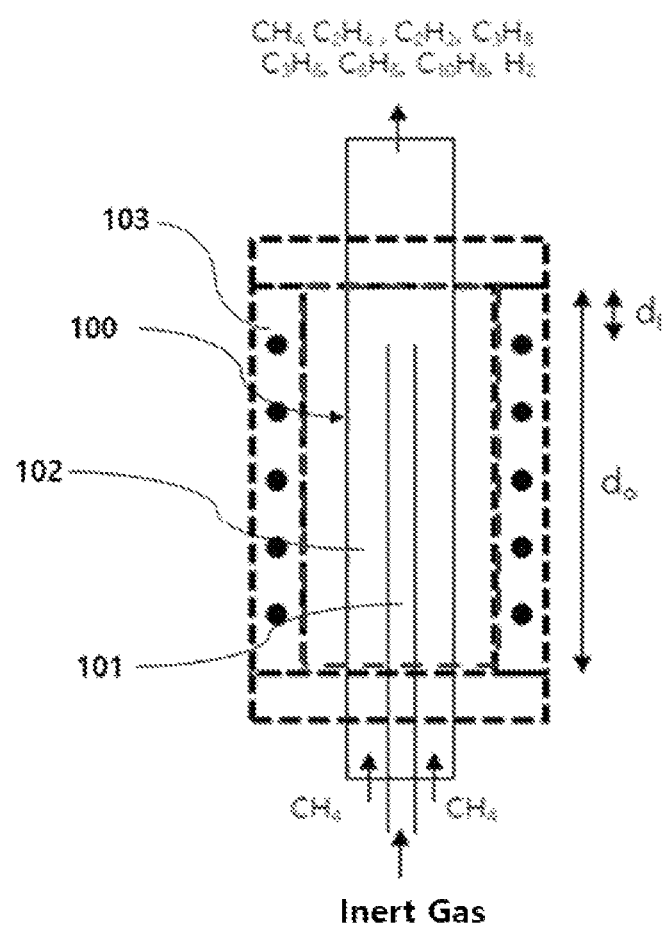

REACTORS FOR PREPARING VALUABLE HYDROCARBONS AND HYDROGEN FROM METHANE THROUGH NON-OXIDATIVE PYROLYSIS

CROSS-REFERENCE TO RELATED APPLICATION

This application claims priority to Korean Patent Application No. 10-2020-0039791 filed Apr. 1, 2020, the disclosure of which is hereby incorporated by reference in its entirety.

BACKGROUND OF THE INVENTION

Field of the Invention

This disclosure relates to reactors for preparing valuable hydrocarbons from methane through non-oxidative pyrolysis. More specifically, this disclosure relates to a pyrolysis reaction system and a direct non-oxidative methane coupling process using the same by which it is possible to achieve high selectivity for $C_{\leq 10}$ hydrocarbons and at the same time to suppress coke formation while maintaining desirable conversion in the course of direct conversion of methane into $C_2$ or higher hydrocarbons through non-oxidative pyrolysis.

Description of the Related Art

Methane is the most abundant compound in natural gas and contains a carbon content as much as twice the carbon contents in a known fossil fuel source. Specifically, natural gas reserves have been reported to be more than a total of coal and oil reserves. As the coal and oil are gradually depleted, availability of natural gas significantly affects the global energy balance. Hence, natural gas such as methane is available for 20 years or more, compared to petroleum (oil) resources, and is regarded as the most feasible alternative raw material which can substitute for oil in the era of oil resource depletion and high oil price, and thus studies for converting methane into more useful chemicals are being intensively conducted and related technologies are being developed.

In order to increase value of natural gas, the natural gas needs to be liquefied for storage and transportation; however, when a production site is distant from a consumption site, a significant part of natural gas produced at the production site is transmitted back into the underground or is burned. Hence, in order to utilize natural gas, that is, methane, usefully, converting methane into hydrocarbons, which are easily transported and stored, is demanded.

Both direct conversion methods and indirect conversion methods have been studied to convert methane into heavier hydrocarbons. The indirect conversion method involves production of synthesis gas primarily through steam reforming or the like, whereas the direct conversion method is performed without an intermediate step such as a step of generating synthesis gas. Currently, commercially available processes for methane to valuable chemicals involve the synthesis of hydrocarbon compounds from synthesis gas through partial oxidation of methane. For example, in the Fischer-Tropsch process, hydrocarbon compounds are produced from synthesis gas with a metal catalyst (Co and Fe). However, the indirect conversion method carries several steps with low reaction efficiency resulting in being difficult to secure economic values due to high costs of processes operated at high temperatures and pressures.

In this respect, methods for directly producing valuable chemicals from methane without involving the production of synthesis gas have been being developed. As a representative direct methane conversion method, the production of ethylene through oxidative coupling of methane has been reported. For example, techniques for promoting oxidative coupling of methane using a transition metal catalyst so as to increase methane conversion or selectivity for $C_{2+}$ hydrocarbons were published (e.g., Korean Patent Publication No. 2018-0113448). Despite the use of catalysts, coke is formed on a surface of the catalyst under a high-temperature and high-pressure condition. In particular, as the methane conversion increases, the selectivity for coke increases, resulting in a dramatic decrease in the selectivity for hydrocarbons. Thus, the reaction condition needs to be carefully controlled.

The reaction where heavier hydrocarbons are coupled through pyrolysis of methane has a particular problem that a by-product such as coke tends to be formed under a high-temperature reaction condition. Specifically, a significant portion of methane is converted into $C_2$ hydrocarbons (ethylene and/or acetylene) or remains unreacted, and the coke formation rapidly occurs in accordance with Reaction Formula (1) below through a chain reaction during the high-temperature pyrolysis.

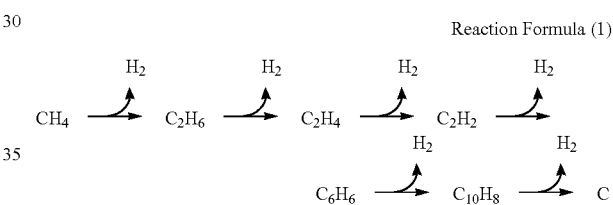

Reaction Formula (1)

In the case of coke deposition in a reactor, the reaction equipment has to be shut down regularly or irregularly to eliminate the coke deposits, which is not desirable in terms of facility maintenance.

In order to solve the above-mentioned problems related to the coke formation, studies for finding an optimal reaction condition with the suppression of coke formation, have been carried out. However, it is limited to inhibit the coke formation only through the control of the reaction condition, thus it is desirable to fundamentally solve the problems by designing the pyrolysis reactor.

Hence, a reactor or a reaction system is required in the synthesis of heavier hydrocarbons from methane (e.g., coupling) together with achieving the increase in selectivity toward more valuable hydrocarbons, compared to methane, at good methane conversion and simultaneously suppressing a large amount of coke deposits generated by the conventional pyrolysis reactor.

SUMMARY OF THE INVENTION

In an embodiment according to this disclosure, there is provided a design structure of a long-term operable reactor by which it is possible to increase the conversion for target hydrocarbons while inhibiting the coke formations during the direct conversion of methane through non-oxidative pyrolysis.

In addition, in another embodiment according to this disclosure, a method is provided for performing direct non-oxidative coupling of methane, which is capable of maximizing the selectivity toward hydrocarbons and minimizing the coke formation without requirement for sophisticated control during the catalytic reaction.

According to a first aspect of this disclosure, there is provided a pyrolysis system comprising a double-tube reactor having:

an inner tube;

an outer tube disposed to concentrically surround the inner tube; and a heater member that is disposed at an outer side of the outer tube along a length of the outer tube and supplies heat through the outer tube, wherein the inner tube operates for a supply source of inert gas, while a space (e.g., annular space) defined between the inner tube and the outer tube operates for a supply source of methane-containing gas, the heater member in the double-tube reactor has an arrangement relationship represented by Formula (1) with each of the outer tube and the inner tube, and flowing of the inert gas through the inner tube has a relationship represented by Formula (2) with flowing of the methane-containing gas through the space defined between the inner tube and the outer tube, $$d_1/d_0 < 0.5 \quad (1)$$

wherein $d_0$ represents a length of the outer tube to which heat supplied from the heater member is directly radiated, and $d_1$ represents a distance from an end portion of the outer tube to which heat supplied from the heater member is directly radiated to an end portion of the inner tube.

$$v_1/v_0 \geq 0.5 \quad (2)$$

wherein $v_1$ represents a volumetric flow rate of the inert gas flowing in the inner tube, and $v_0$ represents a volumetric flow rate of the methane-containing gas flowing in the outer tube.

According to an illustrative embodiment, a ratio of an inner diameter to an outer diameter of the outer tube may be in a range of 0.38 to 0.92, and a ratio of an inner diameter to an outer diameter of the inner tube may be in a range of 0.38 to 0.92.

According to a second aspect of this disclosure, there is provided a method for performing direct non-oxidative methane coupling, which comprises:

a) providing a pyrolysis system comprising a double-tube reactor having an inner tube, an outer tube disposed to concentrically surround the inner tube, and a heater member disposed at an outer side of the outer tube along a length of the outer tube; and b) performing a pyrolysis reaction by supplying heat from the heater member via the outer tube and heating while supplying inert gas through the inner tube and methane-containing gas through a space (e.g., annular space) defined between the inner tube and the outer tube, wherein the heater member in the double-tube reactor has an arrangement relationship represented by Formula (1) with each of the outer tube and the inner tube, and flowing of the inert gas through the inner tube has a relationship represented by Formula (2) with flowing of the methane-containing gas through the space defined between the inner tube and the outer tube, $$d_1/d_0 < 0.5 \quad (1)$$

wherein $d_0$ represents a length of the outer tube to which heat supplied from the heater member is directly radiated, and $d_1$ represents a distance from an end portion of the outer tube to which heat supplied from the heater member is directly radiated to an end portion of the inner tube.

$$v_1/v_0 \geq 0.5 \quad (2)$$

wherein $v_1$ represents a volumetric flow rate of the inert gas flowing in the inner tube, and $v_0$ represents a volumetric flow rate of the methane-containing gas flowing in the outer tube.

According to an illustrative embodiment, step b) described above may be performed under a temperature condition chosen in a range of 900° C. to 1,300° C.

According to an illustrative embodiment, a residence time of the methane-containing gas in the double-tube reactor may be adjusted in a range of 0.5 seconds to 10 seconds.

According to an illustrative embodiment, the inert gas may be at least one selected from the group consisting of helium, nitrogen, argon, neon, xenon, carbon monoxide, carbon dioxide, and steam.

According to an illustrative embodiment, b) described above may be performed under a pressure condition chosen in a range of 0.1 bar to 5 bar.

BRIEF DESCRIPTION OF THE DRAWING

FIG. 1 is a view schematically illustrating a process of performing a pyrolysis reaction of methane using a pyrolysis system equipped with a double-tube reactor according to an illustrative embodiment.

DETAILED DESCRIPTION OF THE PREFERRED EMBODIMENTS

The present invention can be realized in accordance with the following description, overall. The following description is to be understood as description of preferred embodiments of the invention, and the invention does not have to be limited thereto. In addition, the accompanying drawing is provided for easy understanding, and it should be understood that the invention is not limited thereto.

Terms used in this specification can be defined as follows.

The term "coke" can refer to hydrocarbons having a low hydrogen content, and specifically, a solid carbon residual by-product.

The term "coupling" can refer to a chemical reaction in which two identical molecules react with each other to form a single dimer, in a narrow sense.

The term "methane coupling" can be understood to include not only $C_2$ hydrocarbons (for example, ethane, ethylene, acetylene, and the like) but also hydrocarbon ($C_2$) dimers (for example, propane, butane, benzene, naphthalene, and the like) having two or more carbon atoms, hydrogen ($H_2$), or the like from methane. For example, methane can be activated to form methyl radicals and can be converted into ethane, and then the thus-converted ethane can be transformed into ethylene through dehydrogenation. Additionally, the obtained ethylene can be converted into acetylene through the dehydrogenation reaction, and further heavier hydrocarbons can be formed through generation of hydrocarbon radicals.

The term "pyrolysis" can refer to a reaction in which hydrocarbons are decomposed when being exposed to heat or the like without addition of oxygen or an oxygen-containing reactant and, in this disclosure, can include any reaction in which heat is applied to a compound such that the compound is converted into one or more other materials.

The term "$C_{\leq 10}$ hydrocarbon compounds" can refer to hydrocarbon compounds having 10 or less carbon atoms, and examples thereof can be ethane ($C_2H_6$), ethylene ($C_2H_4$), acetylene ($C_2H_2$), benzene ($C_6H_6$), propane ($C_3H_8$), propylene ($C_3H_6$), butane ($C_4H_{10}$), butylene ($C_4H_8$), benzene ($C_6H_6$), toluene ($C_7H_8$), xylene ($C_8H_{10}$), naphthalene ($C_{10}H_8$), or a mixture thereof.

Overall Disclosure

According to an embodiment of this disclosure, there is provided a pyrolysis reaction system, where a reaction of methane gas is carried out at a high temperature to form a dimer.

Methane is a nonpolar molecule having a structure similar to a stable structure of inert gas, has C—H bonding energy of 435 kJ/mol, and has high thermodynamic stability. Such high chemical and thermodynamic stability is known to be a factor that methane is difficult to be converted into various compounds. In this respect, the pyrolysis system according to the embodiment provides a solution by which methane can be effectively converted into heavier hydrocarbons through a direct non-oxidative coupling reaction.

According to the embodiment, methane is activated to become methyl radicals during the direct non-oxidative methane coupling through pyrolysis, and then a radical reaction is performed. Here, in order to control a radical reaction in a zone where a large amount of coke is generated in the tube-type reactor operating at a high temperature, a double-tube type reactor equipped with a separate tube (inner tube) separated from an outer tube with a predetermined gap therebetween in an inside space of a tube-type reactor for pyrolysis is applied, and while inert gas is introduced through the inner tube, methane-containing gas is introduced through a space defined between the outer tube and the inner tube. Here, the reactor can be designed to have the inner tube that satisfies a particular dimension or a positional relationship with the outer tube. In addition, flowing characteristics (e.g., flow rate) of gas flowing in each of the inner tube and the outer tube can be adjusted, and thereby coke can be effectively inhibited from being generated in a pyrolysis zone.

A design of the direct non-oxidative methane coupling reactor enables the selectivity for $C_{\leq 10}$ hydrocarbons to be maximized while the conversion of methane is maintained at a high level without accurate control generally demanded in a case of using a catalyst, and thus a long-term operation of the reactor can be achieved.

Double-Tube Type Pyrolysis Reactor

FIG. 1 schematically illustrates a process of performing a pyrolysis reaction of methane using the pyrolysis system equipped with a double-tube reactor according to an illustrative embodiment.

With reference to the drawing, a reactor 100 in the pyrolysis system is a double-tube reactor and can have an inner tube 101 and an outer tube 102 disposed to surround the inner tube 101 with a predetermined gap therebetween. Here, heat required for the pyrolysis is supplied from a heater member 103, and the heater member 103 is disposed at an outer region of the outer tube 102 along a length of the outer tube 102, as illustrated. Hence, in the illustrated embodiment, the heat require for an endothermic reaction can be supplied from an external heat supply source (that is, heater member) via the outer tube 102 to the pyrolysis zone (or region) of the double-tube reactor 100.

According to the illustrated embodiment, the inner tube 101 operates to separate supply source of inert gas (not illustrated) in the system, while a space defined between the inner tube 101 and the outer tube 102 operates for a supply source of methane gas (not illustrated).

According to the illustrative embodiment, the inner tube 101 and the outer tube 102 can be made of the same material or materials different from each other. In this regard, each of the inner tube 101 and the outer tube 102 can be configured of any material having coke resistance properties.

According to the illustrative embodiment, a material of each of the inner tube 101 and the outer tube 102 can be at least one selected from the group consisting of alumina ($Al_2O_3$), silica ($SiO_2$), silicon carbide (SiC), boron nitride (BN), and an iron-chromium-aluminum (FeCrAl) alloy. More specifically, each of the inner tube 101 and the outer tube 102 can have a surface made of at least one material selected from the group consisting of alumina, silica, silicon carbide, boron nitride, and an iron-chromium-aluminum alloy.

According to the illustrative embodiment, when the material of each of the inner tube 101 and the outer tube 102 is alumina, the thermal conductivity thereof can be about 10 to 30 W/m·K (specifically, about 12 to 25 W/m·K, and more specifically about 15 to 22 W/m·K) at a direct non-oxidative methane coupling temperature of about 900° C. to 1,300° C., for example. When the material is an iron-chromium-aluminum alloy, the thermal conductivity thereof can be about 10 to 35 W/m·K (specifically, about 17 to 32 W/m·K, and more specifically about 20 to 30 W/m·K).

According to the illustrative embodiment, alumina, silica, silicon carbide, boron nitride (BN), and/or an iron-chromium-aluminum (FeCrAl) alloy which are used as a material or a surface material of each of the inner tube 101 and the outer tube 102 can serve as a catalyst of the direct non-oxidative methane coupling (or dimerization). According to a specific embodiment, a material of each of the inner tube 101 and the outer tube 102 can be alumina, and thus a catalytic surface for the direct non-oxidative methane coupling reaction can be provided.

According to the illustrative embodiment, a ratio of an inner diameter to an outer diameter of the outer tube 102 can be in a range of about 0.38 to 0.92, specifically about 0.69 to 0.9, and more specifically about 0.7 to 0.84, and a ratio of an inner diameter to an outer diameter of the inner tube 101 can be in a range of about 0.38 to 0.92, specifically about 0.67 to 0.9, and more specifically about 0.7 to 0.84.

According to an illustrative embodiment, a ratio of the outer diameter of the inner tube to the inner diameter of the outer tube can be in a range of 0.01 to 0.83, specifically about 0.46 to 0.75, and more specifically about 0.5 to 0.67, for example. In this regard, a gap or a space between the outer diameter of the inner tube and the inner diameter of the outer tube can function as a flowing passage of the methane-containing gas, and thus the ratio of the outer diameter of the inner tube to the inner diameter of the outer tube can be appropriately adjusted with consideration for a flow (volumetric flow rate) of inert gas which is introduced into the inner tube, a flow (volumetric flow rate) of methane-containing gas in the methane-containing gas flowing passage, a ratio between these flows, and the like.

According to the illustrated embodiment, the heater member 103 is provided at an outer side of the outer tube along the length of the outer tube. Here, as long as the heater member 103 can supply heat sufficient for the pyrolysis, specifically, the endothermic reaction in which free methyl radicals as activated forms of methane are formed and dehydrogenation occurs, into a reaction zone (region) via the outer tube 102, any heating means known in the related art can be employed as the heater member. According to the illustrative embodiment, the heater member 103 can be a heat exchanger, a heating coil, and a combustion heater, and can be used alone or in a combination thereof.

In the reaction system according to the illustrated embodiment, the heater member 103 can be disposed to directly radiate heat for the pyrolysis to the outer tube 102. In this case, a portion radiated with heat by the heater member can be the entire length of the outer tube 102 or a part of the entire length of the outer tube 102.

With reference to FIG. 1, the inner tube 101 is provided to have a length equal to or shorter than a length $d_0$ of the outer tube 102 to which heat is directly radiated from the heater member 103 in the reaction zone (double dotted line) of the pyrolysis system (that is, the inner tube is extended to an end portion of the outer tube or is extended to a position which does not reach the end portion in a direction in which a pyrolysis product is discharged). As a result, a distance $d_1$ defined as from the end portion of the outer tube having a length $d_0$ to an end portion of the inner tube can be formed.

In this regard, the heater member 103 in the double-tube reactor 100 has an arrangement relationship represented by Formula 1 as below with each of the outer tube 102 and the inner tube 101.

$$d_1/d_0 < 0.5 \qquad (1)$$

wherein $d_0$ represents the length of the outer tube to which heat supplied from the heater member is directly radiated, and $d_1$ represents a distance from the end portion of the outer tube to which heat supplied from the heater member is directly radiated to the end portion of the inner tube.

According to the illustrated embodiment, $d_1/d_0$ is adjusted to be lower than 0.5. This is because a fluid flowing into the inner tube can cool a fluid flowing into the outer tube, thus, activation of methane can be hindered when $d_1/d_0$ is higher than a certain level, and thereby the selectivity for $C_{\leq 10}$ hydrocarbons can be reduced.

In this regard, a ratio of $d_1/d_0$ can be further adjusted in a range lower than about 0.4, and more specifically lower than about 0.35, with consideration for other reaction conditions (for example, the flow rate of gas which is introduced into each of the inner tube and the outer tube, a reaction temperature, or the like) during the pyrolysis reaction, and the ratio can be set to 0 depending on the reaction conditions (that is, the inner tube has the same length as that of the outer tube to which heat from the heater member is directly radiated).

The hydrocarbons and coke generation reaction through the direct non-oxidative methane coupling reaction is a continuous radical reaction. Methane flowing through the outer tube is converted into methyl radicals through pyrolysis at a high reaction temperature (for example, about 1,050° C.), and the converted methyl radicals are continuously bound and/or decomposed to form ethane, ethylene, and acetylene sequentially. In addition, as a concentration of acetylene increases along a direction of the reactor, aromatic hydrocarbons can be formed. Aromatic hydrocarbons function as coke generation seeds. Thus, when aromatic hydrocarbons start to be formed, coke is quickly formed in the reactor.

As described above, in the direct non-oxidative methane coupling reaction, which is a continuous reaction, a concentration of a product differs in a flowing direction of a fluid in a reactor. Hence, the selectivity for ethane is high at a front portion of the zone or region in which the converted product from methane is formed in the reactor, and the selectivity for coke is high at a rear portion thereof. Thus, in order to inhibit coke from being generated at the rear portion of the reactor, it is advantageous to end the pyrolysis reaction by quenching the reaction (i.e., rapidly decreasing the reaction temperature) at the portion (or position) where the selectivity for hydrocarbon products except for aromatic hydrocarbons is maximized.

Referring to FIG. 1 again, a feedstock containing methane is introduced into the pyrolysis reaction system through the space between the inner tube and the outer tube of the double-tube reactor. According to the illustrated embodiment, in order to reduce generation of coke during the conversion reaction of methane, the reactor is designed such that flowing of inert gas through the inner tube 101 has a relationship represented by Formula 2 below with flowing of methane-containing gas through the space between the outer tube 102 and the inner tube 101.

$$v_1/v_0 \geq 0.5 \qquad (2)$$

where $v_1$ represents a volumetric flow rate of the inert gas flowing in the inner tube, and $v_0$ represents a volumetric flow rate of the methane-containing gas flowing in the outer tube.

As described above, a ratio of $v_1/v_0$ is adjusted to be 0.5 or higher, because a quenching effect of a fluid flowing in the inner tube can be reduced when the ratio of $v_1/v_0$ is lower than a certain level. Regarding methane flowing through the space between the outer tube and the inner tube of the reactor, the conversion of methane gradually increases in the flowing direction due to an increase in temperature of the fluid, and at the same time, a temperature of inert gas flowing through the inner tube of the reactor also increases. Here, when a difference between a temperature at the end portion of the inner tube and a temperature of methane is too small due to a low ratio of $v_1/v_0$, the quenching effect can be reduced, and the selectivity for $C_{>10}$ hydrocarbons can increase.

According to the illustrative embodiment, the ratio of $v_1/v_0$ can be appropriately adjusted specifically in a range of about 1 to 3, and more specifically in a range of about 1.5 to 2.5, depending on other reaction conditions (for example, a reaction temperature or the like). In a specific embodiment, the ratio of $v_1/v_0$ can be adjusted to be about 2.

As described above, methane-containing gas, which is a feedstock, is injected or introduced through the space between the inner tube and the outer tube in a double-tube type pyrolysis reactor, and inert gas is together supplied to a predetermined point or position within the reaction zone through the inner tube. In this manner, an activated form (that is, free methyl radical) of methane is stably converted into $C_{\leq 10}$ hydrocarbons, particularly, into ethane, ethylene, and/or acetylene, and at the same time, it is possible to inhibit an additional chain extension reaction from being performed to the extent that coke is formed.

Direct Non-Oxidative Coupling Process of Methane Through Pyrolysis

According to another embodiment of this disclosure, there is provided a process of synthesizing heavier hydrocarbons, specifically, one or two or more $C_{\leq 10}$ hydrocarbons, through the direct non-oxidative coupling reaction of methane using the double-tube type pyrolysis reactor described above.

With reference to FIG. 1, inert gas is introduced through the inner tube 101 in the double-tube reactor 100, while methane-containing gas is supplied through the space between the inner tube 101 and the outer tube 102. Along with this, the reaction zone is heated in a way of directly radiating heat to the outer tube 102 from the heater member 103. As a result, the methane-containing gas can be converted into $C_2$ saturated/unsaturated compound (for example, ethane, ethylene, acetylene, or the like), a $C_3$ saturated/unsaturated compound (for example, propane, propylene, or the like), and/or aromatic hydrocarbons (for example, benzene, toluene, xylene, naphthalene, or the like), for example, as illustrated. In addition, a reaction product can inevitably contain unconverted methane, a by-product such as $C_{>10}$ hydrocarbons and can further contain hydrogen ($H_2$) generated through a dehydrogenation reaction.

According to the illustrated embodiment, the feedstock (that is, the methane-containing gas) which is introduced through the space between the inner tube 101 and the outer tube 102 from a supply source can be typically at least one selected from liquefied natural gas, natural gas, mixed gas having methane as a main component (specifically, at least about 50 vol. %). In this regard, natural gas mainly contains methane and can further contain any hydrocarbon gas component or components other than methane (for example, at least one selected from the group consisting of ethane, propane, and heavier hydrocarbons) and/or dilution gas (for example, at least one selected from the group consisting of nitrogen, oxygen, carbon dioxide, helium, and hydrogen sulfide).

According to the illustrative embodiment, the concentration of methane in the feedstock gas can be, for example, at least about 60 vol. %, specifically at least about 80 vol. %, more specifically at least about 90 vol. %, and can be about 100 vol. % (that is, pure methane) in some cases; however, this can be understood as an illustrative purpose. In addition, the amount of the hydrocarbon component or components other than methane can be, for example, about 40 vol. % or lower, specifically about 20 vol. % or lower, and more specifically about 10 vol. % or lower.

Besides, a dilution gas component content in the feedstock gas can be, for example, in a range of about 20 vol. % or lower, specifically about 10 vol. % or lower, and more specifically about 5 vol. % or lower. In a specific embodiment, one or more species selected from the group consisting of nitrogen in a range of, for example, about 15 vol. % or lower (specifically about 10 vol. % or lower, and more specifically about 5 vol. % or lower), oxygen in a range of, for example, about 0.2 vol. % or lower (specifically about 0.1 vol. % or lower, and more specifically about 0.05 vol. % or lower), carbon dioxide in a range of, for example, about 8 vol. % or lower (specifically about 5 vol. % or lower, and more specifically about 2 vol. % or lower), helium in a range of, for example, about 2 vol. % or lower (specifically about 1 vol. % or lower, and more specifically about 0.5 vol. % or lower), and hydrogen sulfide in a range of, for example, about 5 vol. % or lower (specifically about 3 vol. % or lower, and more specifically about 1 vol. % or lower) can be contained as dilution gas components.

According to the illustrated embodiment, the inert gas is introduced into the pyrolysis reaction system through the inner tube 101, and the inert gas can be selected from a type of gas having chemically stable properties without being involved in the direct non-oxidative methane coupling reaction. According to the illustrative embodiment, the inert gas can be any selected from the group consisting of helium, nitrogen, argon, neon, xenon, carbon monoxide, carbon dioxide, steam, or a mixture thereof. In a specific embodiment, the inert gas can be helium, and helium is advantageous due to its chemically stable properties.

In the pyrolysis reaction using the double-tube reactor according to the embodiment, the reaction temperature and/or the residence time of the feedstock and design parameters of the reactor described above can affect direct non-oxidative coupling reaction characteristics of methane.

According to the illustrative embodiment, the pyrolysis can be performed under a temperature condition selected in a range of, for example, about 900° C. to 1,300° C., specifically about 1,050° C. to 1,150° C., and more specifically about 1,080° C. to 1,140° C. When the reaction temperature is too low, it is difficult to activate the non-oxidative coupling of methane. On the other hand, when the reaction temperature is too high, the reactor and piping have to be made of special materials so as to endure a high-temperature environment, and thus costs of equipment increases. Further, the reaction temperature can affect the conversion of methane and the selectivity for $C_{\leq 10}$ hydrocarbons, and thus it is advantageous to adjust the reaction temperature in the range described above; however, the present disclosure is not limited thereto.

In the meantime, according to the illustrative embodiment, the residence time of methane-containing gas which is introduced through the space between the inner tube 101 and the outer tube 102 is, for example, about 0.5 seconds to 10 seconds, specifically about 1 second to 5 seconds, and more specifically about 1.5 seconds to 4 seconds. In this regard, when the residence time is too short, a desired methane conversion is not obtained. On the other hand, when the residence time is too long, it is difficult to sufficiently form activated methyl radicals, and thus a yield of $C_{\leq 10}$ hydrocarbons can be reduced. Hence, it can be advantageous to adjust the residence time in the range described above; however, the present disclosure is not limited thereto.

According to the illustrative embodiment, the pyrolysis reaction can be performed under a pressure condition selected in a range of, for example, about 0.1 bar to 5 bar, specifically about 0.1 bar to 2 bar, and more specifically about 0.2 bar to 1 bar. The pyrolysis pressure can affect the conversion of methane and the selectivity to the target product (or products), and thus it can be advantageous to adjust the pyrolysis pressure in the range described above.

According to an exemplary embodiment, as a result of using a double-tube reactor, at the portion in the reaction zone (the distance corresponding to $d_1$, for example) in which a large amount of coke tends to be formed, the converted hydrocarbons are no longer converted into heavier hydrocarbons (for example, $C_{>10}$ hydrocarbons) by inert gas introduced through the inner tube, and thus $C_{\leq 10}$ hydrocarbons can be maintained with stability.

According to an embodiment, as the pyrolysis of the methane-containing gas is performed using the double-tube reactor designed as described above, the conversion of methane can be achieved at, for example, about 10% or higher and specifically in a range of about 10% to 40%. The selectivity for $C_{\leq 10}$ hydrocarbons over such conversion range can be, for example, at least about 65%, specifically at least about 80%, and more specifically at least about 90%. In a particular embodiment, the selectivity for $C_{\leq 10}$ hydrocarbons can be at least about 99%.

According to the illustrative embodiment, among the products converted from methane through the pyrolysis reaction, the selectivity for $C_2$ hydrocarbons (specifically, ethane, ethylene, and/or acetylene) can be, for example, in a range of about 10% to 90% (specifically about 20% to 40% and more specifically about 23% to 36%). In addition, the selectivity for $C_{3-4}$ hydrocarbons can be, for example, in a range of about 10% or lower (specifically about 6% or lower, more specifically about 3% or lower, and most specifically about 1.1% or lower). Besides, the selectivity for $C_{\leq 10}$ aromatic hydrocarbons can be, for example, in a range of about 90% or lower (specifically about 70% or lower and more specifically about 60% or lower). Here, at least one reaction condition can be adjusted such that the selectivity for $C_{>10}$ hydrocarbons which cause the formation of cokes can be, for example, about 40% or lower, specifically about 10% or lower, and more specifically about 1% or lower.

On the other hand, one or two or more $C_{\leq 10}$ hydrocarbons and/or hydrogen contained in a coupling product of methane obtained through the pyrolysis as described above can be separated as individual compounds by using any separation techniques known in the art, for example, distillation, chemical absorption, physical adsorption, dissolution-diffusion, or the like, and the unreacted methane can be recycled to the reaction zone (or region) along with the fresh methane-containing gas. Besides, $C_{>10}$ hydrocarbons are separated and then can be used as a fuel for a combustion heater or can be discarded.

The invention can be more clearly understood with the following examples, and the following examples are provided as examples of the invention and are not provided to limit the scope of the invention.

Example 1

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the fluid was fixed to 2.7 seconds. In addition, helium, which is inert gas, was supplied into the inner tube, and $(v_1/v_0)$ was maintained to 2. The outer tube and the inner tube, respectively, were arranged and fixed to satisfy $(d_1/d_0)=0$. In addition, the reaction temperature was maintained at 1,140° C.

Example 2

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the fluid was fixed to 2.7 seconds. In addition, helium, which is inert gas, was supplied into the inner tube, and $(v_1/v_0)$ was maintained to 2. The outer tube and the inner tube, respectively, were arranged and fixed to satisfy $(d_1/d_0)=0$. In addition, the reaction temperature was maintained at 1, 100° C.

Example 3

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the fluid was fixed to 2.7 seconds. In addition, helium, which is inert gas, was supplied into the inner tube, and $(v_1/v_0)$ was maintained to 2. The outer tube and the inner, respectively, were arranged and fixed to satisfy $(d_1/d_0)=0$. In addition, the reaction temperature was maintained at 1,090° C.

Example 4

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the fluid was fixed to 2.7 seconds. In addition, helium, which is inert gas, was supplied into the inner tube, and $(v_1/v_0)$ was maintained to 2. The outer tube and the inner tube, respectively, were arranged and fixed to satisfy $(d_1/d_0)=0$. In addition, the reaction temperature was maintained at 1,080° C.

Example 5

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the methane fluid was fixed to 2.5 seconds. In addition, helium, which is inert gas, was supplied into the inner tube, and $(v_1/v_0)$ was maintained to 2. The outer tube and the inner tube, respectively, were arranged and fixed to satisfy $(d_1/d_0)=0.18$. In addition, the reaction temperature was maintained at 1,100° C.

Example 6

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the fluid was fixed to 2.7 seconds. In addition, helium, which is inert gas, was supplied into the inner tube, and $(v_1/v_0)$ was maintained to 1. Positions of the outer tube and the inner tube, respectively, were arranged and fixed to satisfy $(d_1/d_0)=0$. In addition, the reaction temperature was maintained at 1,100° C.

Comparative Example 1

Methane and nitrogen were supplied with a volume ratio of 90:10 into an alumina ($Al_2O_3$, outer diameter: 13 mm, and inner diameter: 9 mm) tube, and a residence time of the fluid was fixed to 2.7 seconds. The reaction temperature was maintained at 1, 100° C.

Comparative Example 2

An alumina ($Al_2O_3$, outer diameter: 6 mm, and inner diameter: 4 mm) inner tube was inserted into an alumina ($Al_2O_3$, outer diameter: 13 mm, and inner diameter: 9 mm) outer tube. Methane and nitrogen were supplied with a volume ratio of 90:10 into the outer tube, and a residence time of the fluid was fixed to 2.2 seconds. In addition, helium, which is inert gas, was supplied into the inner tube, and $(v_1/v_0)$ was maintained to 2. The outer tube and the inner tube, respectively, were arranged and fixed to satisfy $(d_1/d_0)=0.53$. In addition, the reaction temperature was maintained at 1, 100° C.

Experimental Example 1

Double-Tube Direct Non-Oxidative Methane Coupling Reaction

The direct non-oxidative methane coupling reaction was performed in accordance with each of Examples 1 to 6 and Comparative Examples 1 and 2. The reaction temperature, the residence time, the volumetric flow rate of methane gas, the volumetric flow rate of inert gas, the reaction pressure, and the position of the inner tube are the same as described in each example.

Gaseous hydrocarbons obtained from the performed reaction were analyzed using 7890A GC manufactured by Agilent Technologies, Inc. Gaseous products were analyzed by a thermal conductivity detector (TCD) connected to an HP-MOLESIEVE 5A column and two flame ionization detectors (FID) connected to an HP-PLOT Q bond column and an HP-5 column, respectively.

$H_2$, $N_2$, $CH_4$, $O_2$, and CO were separated by the HP-MOLESIEVE 5A column and were detected by the TCD, and the conversion rate was calculated as an integrated $CH_4$ area vs. an integrated $N_2$ area which is an internal standard.

$C_1$ to $C_5$ light hydrocarbons were separated by the HP-PLOT Q bond column and were detected by the FID, and $C_6$ to $C_{10}$ hydrocarbons were separated by the HP-5 column and were detected by the FID. Compounds having eleven or more carbon atoms were regarded as coke. Reaction results are provided in the table to be provided below.

Experimental Example 2

Single-Tube Direct Non-Oxidative Methane Coupling Reaction

The direct non-oxidative methane coupling reaction was performed in accordance with Comparative Example 1. The reaction temperature, the stay time, the volumetric flow of methane gas, the volumetric flow of inert gas, the reaction pressure, and the position of the inner tube are the same as described in Comparative Example 1.

Gaseous hydrocarbons obtained from the performed reaction were analyzed using 7890A GC manufactured by Agilent Technologies, Inc. Gaseous products were analyzed by the thermal conductivity detector (TCD) connected to the HP-MOLESIEVE 5A column and two flame ionization detectors (FID) connected to the HP-PLOT Q bond column and the HP-5 column, respectively.

$H_2$, $N_2$, $CH_4$, $O_2$, and CO were separated by the HP-MOLESIEVE 5A column and were detected by the TCD, and the conversion rate was calculated as an integrated $CH_4$ area vs. an integrated $N_2$ area which is the internal standard.

$C_1$ to $C_5$ light hydrocarbons were separated by the HP-PLOT Q bond column and were detected by the FID, and $C_6$ to $C_{10}$ hydrocarbons were separated by the HP-5 column and were detected by the FID. Compounds having eleven or more carbon atoms were regarded as coke. Reaction results are provided in the table to be provided below.

The table provides the methane conversion depending on the reaction temperature and the selectivity for ethane, ethylene, acetylene, $C_{3-4}$, benzene, $C_{7-9}$, naphthalene hydrocarbons and cokes in the double-tube reactor.

In Example 1, when the double-tube reactor was used with the reaction temperature of 1,140° C., the methane conversion of 39.4% and the selectivity of 89.9% for $C_{\leq 10}$ hydrocarbons, respectively, were obtained. In Example 2, when the double-tube reactor was used with the reaction temperature of 1,100° C., the methane conversion of 25.3% and the selectivity of 93% for $C_{\leq 10}$ hydrocarbons, respectively, were obtained. In Example 3, when the double-tube reactor was used with the reaction temperature of 1,090° C., the methane conversion of 17.5% and the selectivity of 98.5% for $C_{\leq 10}$ hydrocarbons, respectively, were obtained. In addition, in Example 4, when the reaction temperature was 1,080° C., the methane conversion of 13.4% and the selectivity of 90.1% for $C_{\leq 10}$ hydrocarbons, respectively, were obtained.

When comparing Examples 2 to 6, where the same reaction condition was maintained while the ratio of $v_1/v_0$ was changed, a difference in methane conversion was not significant; however, more desirable results of the selectivity for $C_{\leq 10}$ hydrocarbons were observed in Example 2 in which the ratio of $v_1/v_0$ was adjusted to 2.

In a case of Comparative Example 1 to which the double-tube reactor was not applied, the methane conversion was slightly higher than that in Examples 2 to 6; however, it was observed that a large amount of $C_{>10}$ hydrocarbons, which induce the coke formation, were contained in a product. Hence, it was concluded that a high yield of $C_{\leq 10}$ hydrocarbons can be obtained by using the double-tube type reactor.

On the other hand, the product distribution was analyzed with the reaction temperature varied (Examples 1 to 4; ratio of $d_1/d_0$:0 and ratio of $v_1/v_0$:2). When the reaction temperature was set to 1,140° C. (Example 1), the methane conversion of 39.4% and the selectivity of 89.9% for $C_{\leq 10}$ hydrocarbons, respectively, were obtained, which corresponds to the highest yield (35.4%) of $C_{\leq 10}$ hydrocarbons.

In addition, the reaction was performed and analyzed on the condition of fixing $v_1/v_0$ to 2, while varying $d_1/d_0$. In this experiment, when the ratio of $d_1/d_0$ is 0 (Examples 2 and 5 and Comparative Example 2), it was observed that good selectivity for $C_{\leq 10}$ hydrocarbons was obtained in Example 2 ($d_1/d_0$=0), compared to Example 5 ($d_1/d_0$=0.18). As the ratio of $d_1/d_0$ is decreased, a higher yield of $C_{\leq 10}$ hydrocarbons were obtained, particularly when the end portion of the inner tube was positioned at the end portion of the outer tube

TABLE

| Item | Temperature (° C.) | $v_1/v_0$ | $d_1/d_0$ | Conversion (%) | Selectivity (%) | | | | | | | |
|---|---|---|---|---|---|---|---|---|---|---|---|---|
| | | | | | $C_2H_4$ | $C_2H_2$ | C2H6 | $C_3$ to $C_4$ | Benzene | $C_7$ to $C_9$ | Naphthalene | >$C_{10}$ |
| Example 1 | 1140 | 2 | 0 | 39.4 | 7.6 | 15.1 | 0.2 | 2.7 | 24.3 | 6.5 | 33.5 | 10.1 |
| Example 2 | 1100 | 2 | 0 | 25.3 | 12.6 | 19.4 | 0.6 | 4.1 | 25.5 | 3.8 | 27.0 | 7.0 |
| Example 3 | 1090 | 2 | 0 | 17.5 | 14.4 | 17.1 | 1.1 | 4.1 | 21.3 | 7.6 | 32.9 | 1.5 |
| Example 4 | 1080 | 2 | 0 | 13.4 | 16.6 | 17.9 | 1.9 | 5.7 | 20.7 | 7.8 | 28.5 | 0.9 |
| Example 5 | 1100 | 2 | 0.18 | 27.9 | 10.8 | 20.0 | 0.5 | 3.5 | 18.3 | 3.8 | 22.4 | 20.7 |
| Example 6 | 1100 | 1 | 0 | 26.2 | 14.0 | 18.0 | 0.7 | 4.2 | 19.5 | 4.1 | 24.4 | 15.3 |
| Comparative Example 1 | 1100 | — | — | 28.6 | 13.5 | 16.7 | 0.5 | 4.8 | 19.7 | 3.5 | 9.6 | 31.7 |
| Comparative Example 2 | 1100 | 2 | 0.53 | 30.1 | 10.0 | 21.1 | 0.5 | 3.6 | 16.3 | 2.5 | 15.7 | 30.3 | to which the heat supplied from the heater member was directly radiated. On the other hand, when the ratio of $d_1/d_0$ was higher than 0.5 (Comparative Example 2), the selectivity for $C_{\leq 10}$ hydrocarbons was not substantially changed, and thus the beneficial effect of the double-tube reactor was rarely obtained. In addition, in case of fixing the ratio of $v_1/v_0$ to 2, the residence time of methane was slightly reduced as the ratio of $d_1/d_0$ increases (the residence time of methane was 2.7 seconds when $d_1/d_0$=0, and the residence time of methane was 2.2 seconds when $d_1/d_0$=0.53); however, partial pressure of methane was rapidly reduced at the end portion of the inner tube (partial pressure of methane before the end portion of the inner tube was 0.9, and partial pressure of methane after the end portion of the inner tube was 0.3), which is supposed to lead to an increase in the conversion. However, it is difficult to expect a quenching effect on a mixed fluid flowing in the outer tube, to which the heat supplied from the heater member is directly radiated at the same time, with the inert gas flowing in the inner tube. The conversion increases as the ratio of $d_1/d_0$ increases, with ratio of $v_1/v_0$ fixed to 2; however, the selectivity for $C_{\leq 10}$ hydrocarbons was decreased.

According to Examples 1 to 6 and the comparative examples in the table, the selectivity for $C_{\leq 10}$ hydrocarbons can increase to a certain level or higher and at the same time to inhibit coke from being generated while the acceptable methane conversion was retained during the direct conversion of methane into $C_{2+}$ hydrocarbons, by adjusting at least one of (i) the ratio of the flow (or flow rate) of the fluid flowing in the inner tube and the flow (or flow rate) of the fluid flowing in the outer tube in the double-tube reactor and (ii) the relative position (or dimension) of the inner tube in the outer tube.

In the pyrolysis system including the double-tube reactor of the embodiment according to this disclosure, it is possible to prepare hydrocarbons with a high yield while reducing generation of coke in a reaction for converting methane into heavier hydrocarbons (mostly, $C_{\leq 10}$ hydrocarbons) by a direct non-oxidative method. Further, it is possible to maximize the selectivity for hydrocarbons and at the same time to achieve a good conversion even without accurate control generally demanded in the catalytic reactions, and thus the pyrolysis system particularly has an advantage in commercialization.

A person of ordinary knowledge in this field can easily use a simple change or modification of the invention, and either the change or modification can be understood to be included in the scope of the invention.

While the present invention has been described with respect to the specific embodiments, it will be apparent to those skilled in the art that various changes and modifications may be made without departing from the spirit and scope of the invention as defined in the following claims.

What is claimed is:

1. A pyrolysis system comprising a double-tube reactor having:
   an inner tube;
   an outer tube disposed to concentrically surround the inner tube; and
   a heater member that is disposed at an outer side of the outer tube along a length of the outer tube and supplies heat through the outer tube,
   wherein the inner tube operates for a supply source of inert gas, while a space defined between the inner tube and the outer tube operates for a supply source of methane-containing gas,
   the heater member in the double-tube reactor has an arrangement relationship represented by Formula (1) with each of the outer tube and the inner tube, and
   flowing of the inert gas through the inner tube has a relationship represented by Formula (2) with flowing of the methane-containing gas through the space defined between the inner tube and the outer tube, $$d_1/d_0 < 0.5 \tag{1}$$

wherein $d_0$ represents a length of the outer tube to which heat supplied from the heater member is directly radiated, and $d_1$ represents a distance from an end portion of the outer tube to which heat supplied from the heater member is directly radiated to an end portion of the inner tube, $$v_1/v_0 \geq 0.5 \tag{2}$$

wherein $v_1$ represents a volumetric flow rate of the inert gas flowing in the inner tube, and $v_0$ represents a volumetric flow rate of the methane-containing gas flowing in the outer tube.

2. The pyrolysis system according to claim 1, wherein a material of each of the inner tube and the outer tube is at least one selected from the group consisting of alumina ($Al_2O_3$), silica ($SiO_2$), silicon carbide (SiC), boron nitride (BN), and an iron-chromium-aluminum (FeCrAl) alloy.

3. The pyrolysis system according to claim 2, wherein a material of each of the inner tube and the outer tube is alumina.

4. The pyrolysis system according to claim 1, wherein a ratio of an inner diameter to an outer diameter of the outer tube is in a range of 0.38 to 0.92, and a ratio of an inner diameter to an outer diameter of the inner tube is in a range of 0.38 to 0.92.

5. The pyrolysis system according to claim 1, wherein a ratio of an outer diameter of the inner tube to an inner diameter of the outer tube is in a range of 0.01 to 0.83.

6. The pyrolysis system according to claim 1, wherein the heater member is at least one selected from a heat exchanger, a heating coil, and a combustion heater.

7. The pyrolysis system according to claim 1, wherein $d_1/d_0$ is 0.

8. A method for performing direct non-oxidative methane coupling, which comprises:
   a) providing a pyrolysis system comprising a double-tube reactor having an inner tube, an outer tube disposed to concentrically surround the inner tube, and a heater member disposed at an outer side of the outer tube along a length of the outer tube; and
   b) performing a pyrolysis reaction by supplying heat from the heater member via the outer tube and heating while supplying inert gas through the inner tube and methane-containing gas through a space defined between the inner tube and the outer tube,
   wherein the heater member in the double-tube reactor has an arrangement relationship represented by Formula (1) with each of the outer tube and the inner tube, and
   flowing of the inert gas through the inner tube has a relationship represented by Formula (2) with flowing of the methane-containing gas through the space defined between the inner tube and the outer tube, $$d_1/d_0 < 0.5 \tag{1}$$

wherein $d_0$ represents a length of the outer tube to which heat supplied from the heater member is directly radiated, and $d_1$ represents a distance from an end portion of the outer tube to which heat supplied from the heater member is directly radiated to an end portion of the inner tube, $$v_1/v_0 \geq 0.5 \qquad (2)$$

wherein $v_1$ represents a volumetric flow rate of the inert gas flowing in the inner tube, and $v_0$ represents a volumetric flow rate of the methane-containing gas flowing in the outer tube.

9. The method according to claim 8,
wherein the step b) is performed under a temperature condition chosen in a range of 900° C. to 1,300° C.

10. The method according to claim 8,
wherein a residence time of the methane-containing gas in the double-tube reactor is adjusted in a range of 0.5 seconds to 10 seconds.

11. The method according to claim 8,
wherein the step b) is performed under a pressure condition chosen in a range of 0.1 bar to 5 bar.

12. The method according to claim 8,
wherein the methane-containing gas is at least one selected from liquefied natural gas, natural gas, and mixed gas containing methane as a main component.

13. The method according to claim 8,
wherein a concentration of methane in the feedstock gas is at least 60 vol. %.

14. The method according to claim 8,
wherein selectivity for $C_{\leq 10}$ hydrocarbons is at least 65% over methane conversion of 10% to 40% during the pyrolysis reaction.

15. The method according to claim 8,
wherein, among the converted products from methane through the pyrolysis reaction, the selectivity for $C_2$ hydrocarbons is 10% to 90%, the selectivity for $C_3$ to $C_4$ hydrocarbons is 10% or lower, the selectivity for $C_{\leq 10}$ aromatic hydrocarbons is 90% or lower, and the selectivity for $C_{>10}$ hydrocarbons is 40% or lower.

16. The method according to claim 8,
wherein one or two or more $C_{\leq 10}$ hydrocarbon and hydrogen contained in a coupling product of methane obtained through the pyrolysis is separated as individual compounds by using any separation technique selected from the group consisting of distillation, chemical absorption, physical adsorption, or dissolution-diffusion.

17. The method according to claim 8,
wherein the inert gas is any selected from the group consisting of helium, nitrogen, argon, neon, xenon, carbon monoxide, carbon dioxide, steam, or a mixture thereof.

18. The method according to claim 8,
wherein the methane-containing gas further contains any hydrocarbon gas component or components other than methane and/or dilution gas.

19. The method according to claim 18,
wherein the hydrocarbon gas component or components are at least one selected from the group consisting of ethane, propane, and heavier hydrocarbons, and the amount thereof is 40 vol. % or lower.

20. The method according to claim 18,
wherein the dilution gas is at least one selected from the group consisting of nitrogen, oxygen, carbon dioxide, helium, and hydrogen sulfide, and the amount thereof is 20 vol. % or lower.

* * * * *